(12) United States Patent
Wu et al.

(10) Patent No.: US 10,053,727 B2
(45) Date of Patent: Aug. 21, 2018

(54) OLIGONUCLEOTIDE AND METHOD FOR DETECTING TARGET DNA IN A SAMPLE BY FLUORESCENCE FROM COPPER NANOPARTICLES

(71) Applicant: KAOHSIUNG MEDICAL UNIVERSITY, Kaohsiung (TW)

(72) Inventors: Shou-Mei Wu, Kaohsiung (TW); Chung-An Chen, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 180 days.

(21) Appl. No.: 14/738,879

(22) Filed: Jun. 13, 2015

(65) Prior Publication Data

US 2016/0362721 A1    Dec. 15, 2016

(51) Int. Cl.
*C12Q 1/68* (2018.01)
*C12Q 1/686* (2018.01)

(52) U.S. Cl.
CPC .................... *C12Q 1/686* (2013.01)

(58) Field of Classification Search
None
See application file for complete search history.

(56) References Cited

FOREIGN PATENT DOCUMENTS

JP    2007-228803 A    9/2007

OTHER PUBLICATIONS

Chen et al. Analytical Chemistry 2015; 87: 6228-6232 + six pages of Supporting Information.*
Office Action from Taiwan Intellectual Property Office (dated Jun. 21, 2016).
Qing et al., dsDNA-specific fluorescent copper nanoparticles as a "green" nano-dye for polymerization-mediated biochemical analysis, Chem. Commun., 2014, 50:12746-12748.
Hu et al., Double-strand DNA-templated formation of copper nanoparticles as fluorescent probe for label free nuclease enzyme detection, Biosens Bioelectron., Apr. 15, 2013, 42:31-5.
SEQ ID. No. 13 disclosed in Japanese Patent 2007-228803A.

* cited by examiner

*Primary Examiner* — Angela M. Bertagna
(74) *Attorney, Agent, or Firm* — Hannah M. Tien (57) ABSTRACT

The invention provides an oligonucleotide comprising a nucleotide sequence consisting of SEQ ID NO: 1. The invention also provides method for detecting target DNA in a sample with the oligonucleotide.

6 Claims, 9 Drawing Sheets
(7 of 9 Drawing Sheet(s) Filed in Color)

SEQUENCE LISTING

<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: Synthesized DNA for the formation of CuNC

<400> SEQUENCE: 1
ttaccttcct ccgcaatact gca                                           23

```
<210> SEQ ID NO 2
<211> LENGTH: 44
<212> TYPE: DNA
<213> ORGANISM: Artificial Sequence
<220> FEATURE:
<223> OTHER INFORMATION: primer

<400> SEQUENCE: 2
ttaccttcct ccgcaatact gcaagacatg gggcttcatt tttg                    44

<210> SEQ ID NO 3
<211> LENGTH: 43
<212> TYPE: DNA
<213> ORGANISM: Artificial Sequence
<220> FEATURE:
<223> OTHER INFORMATION: primer

<400> SEQUENCE: 3
ttaccttcct ccgcaatact gcatgttagt gcctttcacc ctg                     43

<210> SEQ ID NO 4
<211> LENGTH: 43
<212> TYPE: DNA
<213> ORGANISM: Artificial Sequence
<220> FEATURE:
<223> OTHER INFORMATION: primer

<400> SEQUENCE: 4
ttaccttcct ccgcaatact gcattgccat gtttgtgtcc cag                     43

<210> SEQ ID NO 5
<211> LENGTH: 44
<212> TYPE: DNA
<213> ORGANISM: Artificial Sequence
<220> FEATURE:
<223> OTHER INFORMATION: primer

<400> SEQUENCE: 5
ttaccttcct ccgcaatact gcatgggcag aaaaccaatg attg                    44

<210> SEQ ID NO 6
<211> LENGTH: 45
<212> TYPE: DNA
<213> ORGANISM: Artificial Sequence
<220> FEATURE:
<223> OTHER INFORMATION: primer

<400> SEQUENCE: 6
ttaccttcct ccgcaatact gcaagacaag gtagttggaa ttgtg                   45

<210> SEQ ID NO 7
<211> LENGTH: 43
<212> TYPE: DNA
<213> ORGANISM: Artificial Sequence
<220> FEATURE:
<223> OTHER INFORMATION: primer

<400> SEQUENCE: 7
ttaccttcct ccgcaatact gcaacatgtg acggaagaga tgg                     43
```

OLIGONUCLEOTIDE AND METHOD FOR DETECTING TARGET DNA IN A SAMPLE BY FLUORESCENCE FROM COPPER NANOPARTICLES

CROSS-REFERENCES TO RELATED APPLICATIONS

The sequence listing text file, file name 2417_KMU_US_ST25_2 created Jun. 12, 2015, file size 1503 bytes, is incorporated herein by reference in its entirely.

BACKGROUND OF THE INVENTION

Field of the Invention

The present invention relates to an oligonucleotide and method for detecting target DNA in a sample.

Description of Prior Art

Recently, some noble-metal nanoparticles using DNA as a template for fluorescent metal nanoparticles (NPs) or nanoclusters (NCs) through the binding of metal ions on the DNA and subsequent chemical reduction of the DNA-complexed metal ions. Therefore, DNA-templated fluorescent metal NPs or NCs show great potential as fluorescent probes for biochemical applications due to their advantages of ultrafine size, low toxicity, good biocompatibility, outstanding photophysical properties, as well as facile integration with nucleic acid-based target-recognition abilities and signal amplification mechanisms.

Compared with other existing fluorescent metal NPs, DNA-templated copper NPs (CuNPs), including random double-stranded DNA-templated CuNPs (dsDNA-CuNPs) and poly(thymine)-templated CuNPs (poly T-CuNPs) were reported by Mokhir et al. and Wang et al., respectively. Its formation might be resulted from the high-affinity clustering of $Cu^0$, which is formed through chemical reactions between $Cu^{2+}$ and the reducing agent in solution, on DNA scaffolds. Furthermore, the synthesis of CuNPs is highly efficient, simple, and rapid (about 5 min at room temperature), thus laying a substantial foundation for their widespread applications in biosensing.

SUMMARY OF THE INVENTION

The invention provides an oligonucleotide comprising a nucleotide sequence consisting of SEQ ID NO: 1.

The present invention further provides a method for detecting target DNA in a sample, comprising: providing a forward primer having a 3' portion that complements a first portion of the target DNA and a 5' portion comprising a nucleotide sequence consisting of SEQ ID NO: 1; and a reverse primer having a 3' portion that complements a second portion of the target DNA and a 5' portion comprising the nucleotide sequence consisting of SEQ ID NO: 1; PCR amplifying the target DNA using the forward primer and the reverse primer; adding a solution comprising copper ion and a reducing agent to a product of the PCR amplification to form a copper nanoparticle with the nucleotide sequence consisting of SEQ ID NO: 1, which resulting in fluorescence emission, and detecting the fluorescence emission.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

This invention establishes a sensitive, specific, and easily distinguish the biosensing method for target DNA.

The present invention provides an oligonucleotide comprising a nucleotide sequence consisting of SEQ ID NO: 1. The oligonucleotide further forms a copper nanoparticle with copper ion and emits fluorescence.

The present invention provides a method for detecting target DNA in a sample, comprising: providing a forward primer having a 3' portion that complements, and can hybridize with, a first portion of the target DNA and a 5' portion comprising a nucleotide sequence consisting of SEQ ID NO: 1; and a reverse primer having a 3' portion that complements, and can hybridize with, a second portion of the target DNA and a 5' portion comprising the nucleotide sequence consisting of SEQ ID NO: 1; PCR amplifying the target DNA using the forward primer and the reverse primer; adding a solution comprising copper ion and a reducing agent to a product of the PCR amplification to form a copper nanoparticle with the nucleotide sequence consisting of SEQ ID NO: 1, which resulting in fluorescence emission; and detecting the fluorescence emission.

In one embodiment, the solution comprising copper ion is $CuSO_4$ solution.

In another embodiment, the reducing agent is sodium ascorbate.

In another embodiment, the target DNA is an exon of a target gene.

In another embodiment, the target gene is specific to Duchenne muscular dystrophy (DMD).

Examples

Materials

An oligonucleotide comprising a nucleotide sequence consisting of SEQ ID NO: 1 is incorporated into primers used for exons of target gene (DMD) at 5' end. The resulting oligonucleotide sequences are SEQ ID NO: 2 to SEQ ID NO: 7. All oligonucleotides were ordered from MD Bio, Inc (Taipei, Taiwan), and stored as 100 µM stocks solution in sterilized $H_2O$ at −20° C. 3-morpholinopropane-1-sulfonic acid (MOPS), 3-(N-Morpholino) propanesulfonic acid sodium salt (MOPS sodium salt), (+) Sodium L-ascorbate and $CuSO_4$ were obtained from SigmaAldrich (Sigma, St. Louis, Mo., USA). Sodium chloride (NaCl), hydrochloric acid (HCl), sodium hydroxide (NaOH) were from E. Merck (Darmstadt, Germany). The double-distilled water was obtained from a Milli-Q water system (Millipore, Milford, Mass., USA).

Assay Procedures of PCR and Sensor Preparation

The final volume of PCR was 50 µL containing a mixture of 50 ng of genomic DNA, 2.5 mM dNTP (TaKaRa, Shiga, Japan), 1×PCR buffer (TaKaRa), 160 nM of each primer and 2.0 U of e2TAK DNA polymerase (TaKaRa). The PCR amplification was performed in a Tprofessional Thermocycler (Biometra, Göttingen, Germany) in an initial denaturation step at 95° C. for 10 min, followed by 35 cycles of denaturing at 95° C. for 30 sec, annealing at 59° C. for 15 sec, extension at 72° C. for 30 sec, and a final extension step at 72° C. for 10 min. After PCR cycling was finished, the product was mixed with 10 mM MOPS buffer which contained 150 mM NaCl, then a volume of 4 mM sodium ascorbate and 500 µM $CuSO_4$ were added into the solution to give final a volume of 200 µL and allowed to react for 3 min at room temperature.

Instrumentation

The fluorescence measurements were carried out on an F-4500 fluorescence spectrometer (Hitachi, Japan) with excitation and emission slit set at 5.0 nm and 20 nm, respectively. Scanning speed was set on 240 nm/min. A quartz fluorescence cell with an optical path length of 1.0 cm was used. All measurements were carried out at room temperature unless stated otherwise. The fluorescence emission of the system was recorded from 500 to 650 nm for the excitation wavelength at 345 nm. Transmission electron microscopy (TEM) measurements were performed on a JEOL JEM-1400 transmission electron microscope (JEOL, Japan) operated at 100 kV. TEM samples were prepared onto carbon-coated copper grid substrates, which were then baked in an oven at room temperature.

Real Sample Application

DNA samples from DMD patients, and normal individuals were obtained from Chung-Ho Memorial Hospital, Kaohsiung Medical University. Genomic DNA was collected from peripheral whole blood using Genomic DNA purification kit (ZYMO RESEARCH, Quick-gDNA Mini-Prep-D3024, USA), according to the standard protocol. The ethical approval of this study was obtained from the Institutional Review Board at Kaohsiung Medical University Hospital where participants were recruited and experiments on humans were conducted. Written informed consents were obtained from all participants.

Results

Design and Principle of the Biosensor for the Exon of DMD Detection

Figure 1:
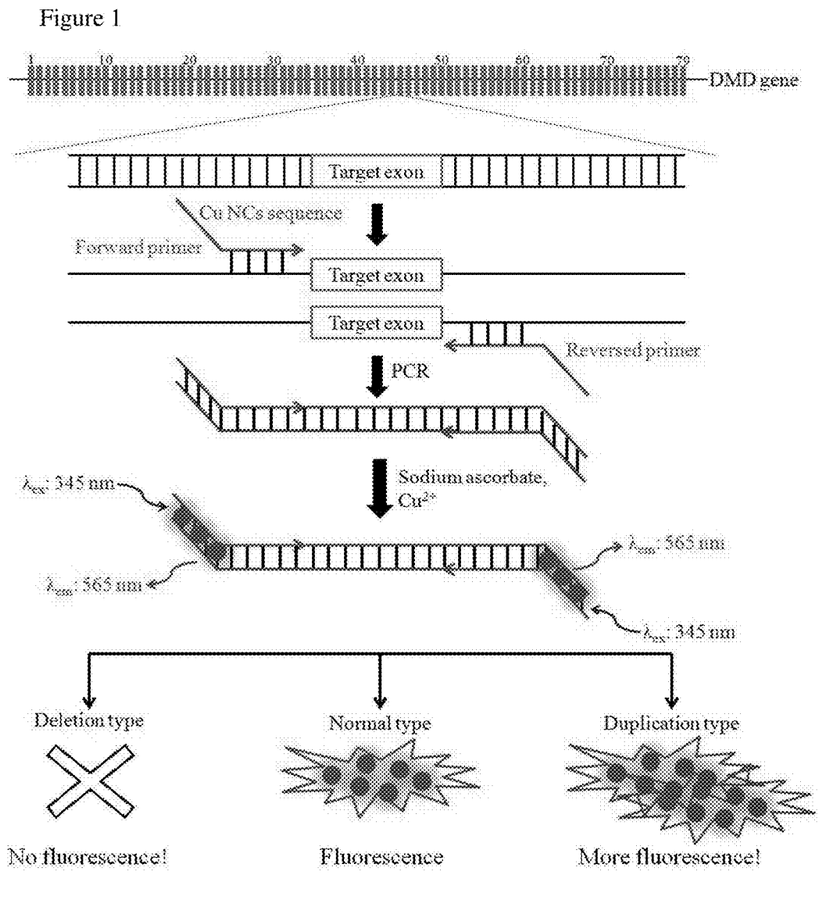
FIG. 1 shows a schematic representation of the sensing procedure for analysis of genotype of PCR reaction based on the dsDNA-CuNCs.

FIG. 1 showed the principle for this study. The sequence to allow formation of dsDNA and fluorescence CuNCs at primer were designed. According to the mechanism, the successful PCR reaction used normal type of genomic DNA, its PCR products could form a stable duplex under present buffer conditions at room temperature which can be used as template for the formation of CuNCs reacted for the reduction of $Cu^{2+}$ by sodium ascorbate. As a result, the formed dsDNA-CuNCs complex would show high fluorescence to be detected. On the other hand, when using deletion type of genomic DNA, the dsDNA-CuNCs could not form because the PCR reaction was not successful result in the fluorescence could not be detected. However, using the duplication type of genomic DNA, the fluorescence would be higher than normal type of genomic DNA. Based on this concept, we could distinguish the deletion or duplication type for the exon more easily.

Figure 2:
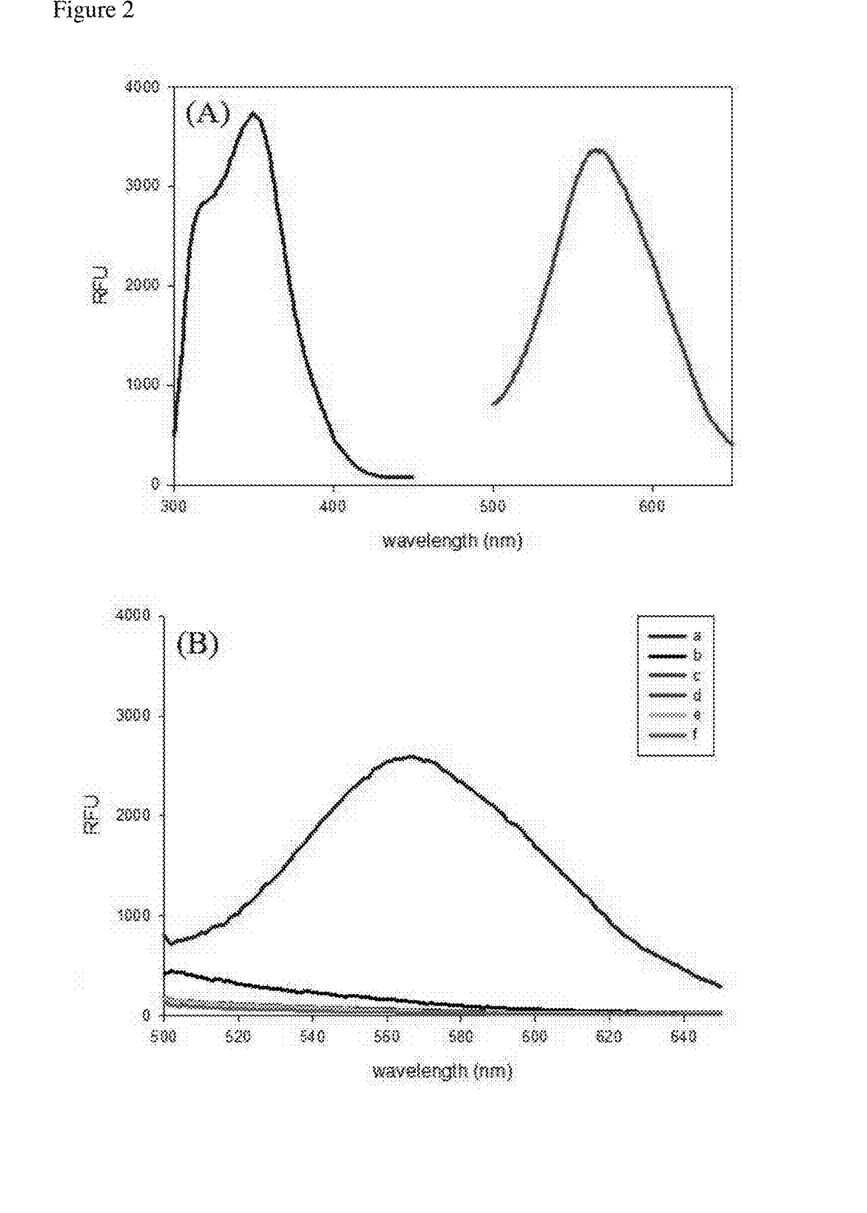
FIG. 2 (A) Fluorescence excitation (blue line) and emission (red line) spectra of the obtained dsDNA-CuNCs; (B) The fluorescence spectra of the sensing system under different conditions: (a) Normal exon 46 (after PCR); (b) blank exon 46 (after PCR); (c) exon 46 forward primer; (d) exon 46 reversed primer; (e) 10 mM MOPS+150 mM NaCl; (f) 10 mM MOPS+150 mM NaCl (no reaction with copper ion and sodium ascorbate); $Cu^{2+}$ concentration: 500 µM; sodium ascorbate concentration: 4 mM.

The dsDNA-templated CuNCs were synthesized according to previous reports. The obtained fluorescent CuNCs have excitation and emission peaks at 345 and 565 nm, respectively (FIG. 2A). Therefore, it had to prove that the formation of dsDNA is necessary for the fluorescence to be produced, the fluorescence spectra of the sensing system under different conditions were tested. From the results, it could be observed that the CuNCs would form in the successful PCR reaction could produce the fluorescent signal. In other conditions, it was not produced the fluorescent signal even if the primer exist at PCR reaction for copper ion and sodium ascorbate in buffer. On the other hand, we also confirmed that the background could not produce any interference in this reaction which enhanced the S/N ratio to perform the signal discrimination (FIG. 2B). It could be indicated that the CuNCs would not form in dsDNA or the presence of ssDNA templates. It provided an excellent selectivity in discriminating dsDNA and ssDNA for dsDNA-CuNCs and helped to distinguish the genotype of deletion and duplication in DMD diagnosis.

Figure 3:
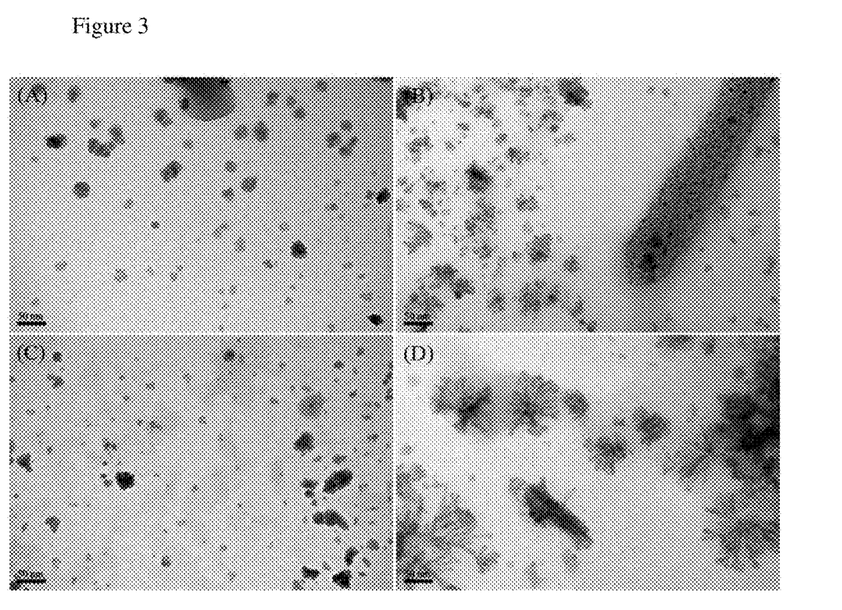
FIG. 3 shows TEM images of dsDNA-CuNCs by real DNA samples: (A) no DNA, (B) normal type, (C) deletion type, (D) duplication type.

The CuNCs were characterized with transmission electron microscope (TEM), we could determine and identify CuNCs could observe which supports the nanoparticles formation with a low concentration of $CuSO_4$. It was observed that in the absence of real DNA samples, the dsDNA-CuNCs formed with about primary particle size of ranging less than 10 nm. TEM image were provided (FIG. 2). From the results, the sintering of CuNCs was significantly presented in FIG. 3. FIG. 3 (A) was no DNA sample reaction with copper ion and sodium ascorbate, we could observe that the CuNCs were produced rarely. For deletion type, some of the CuNCs could observe the sintering action, but it was not seriously which the CuNCs was formed a few (FIG. 3C).

FIG. 3 (B) to 3 (D) were normal, deletion, and duplication type DNA samples after PCR reaction and measured by fluorescent spectrophotometer, respectively. Therefore, we could observe clearly the particle size of CuNCs in FIG. 3 (B), and a seriously sintering action in duplication type sample in FIG. 3 (D). Based on above, we considered that the fluorescence had some relationship with the amounts of CuNCs forming. Therefore, it could prove that the mechanism for this study and the different fluorescent intensity which presented in real DNA samples with normal, deletion, and duplication type (FIG. 3).

Optimization of PCR Reaction

Figure 4:
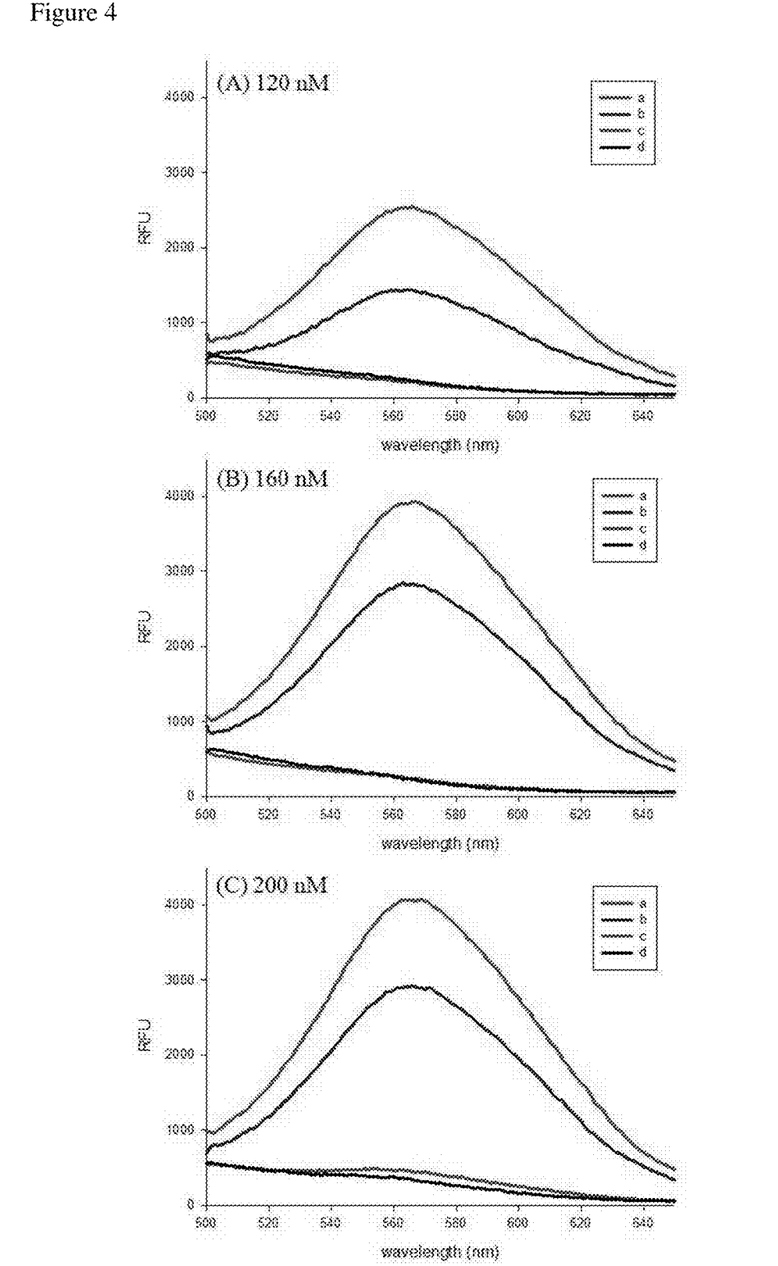
FIG. 4 shows effects of concentration of primers on the fluorescence of the dsDNA-CuNCs within the PCR reaction. (A) 120 nM of forward and reversed primers; (B) 160 nM of forward and reversed primers; (C) 200 nM of forward and reversed primers. (a) Duplication type; (b) Normal type; (c) Deletion type; (d) Blank. Other conditions were same as FIG. 2.

In this invention, PCR reaction played an important role in the amount of the CuNCs sequence. It has been reported that dsDNA can act as an efficient template and the formed CuNCs have excellent fluorescence, whereas ssDNA does not support nanoparticle formation. In this work, the PCR reaction successfully produced the complementary PCR primer to form the dsDNA and make the fluorescent CuNCs. Due to this reason, we optimized the concentration of primer and PCR reaction cycles. FIG. 4 showed the results of primer concentration for this study. According to PCR theory, a successful reaction acquires appropriate concentrations of primers. When not enough primers is added, the PCR products would form the CuNCs and produce weak fluorescence, as shown in FIG. 4 (A). Therefore, we used 160 nM of primers and acquired an optimized result at FIG. 4 (B). FIG. 4 (C) proved that when using too much primer, the blank would also have some fluorescence, because some non-specific PCR products were produce. Finally, the concentration of primer we used 160 nM for the PCR reaction.

Figure 5:
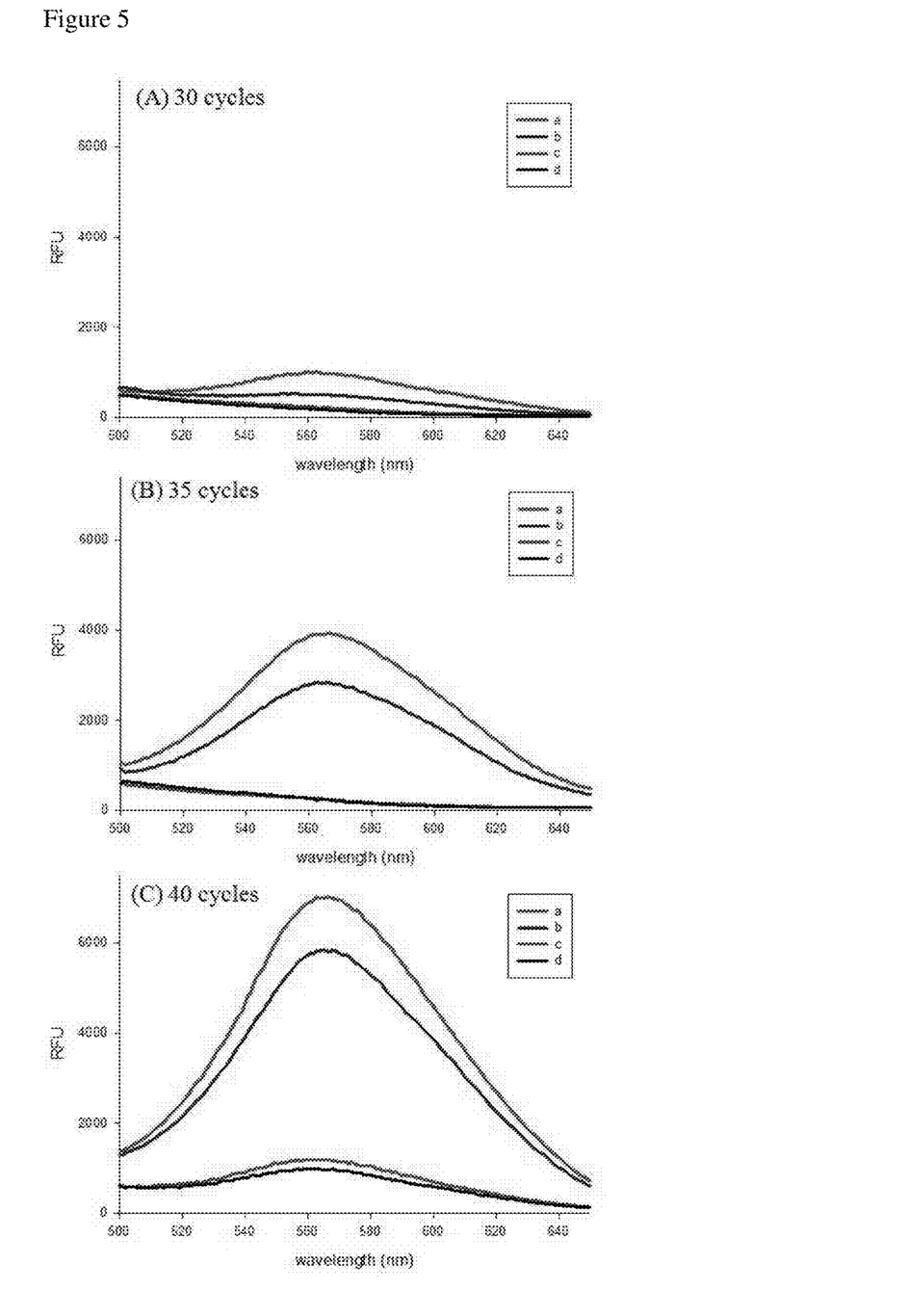
FIG. 5 shows effects of cycle numbers of PCR reaction on the fluorescence of the dsDNA-CuNCs. (A) 30 cycles; (B) 35 cycles; (C) 40 cycles. (a) Duplication type; (b) Normal type; (c) Deletion type; (d) Blank. Other conditions were same as FIG. 2.

The number of PCR cycles influenced the factor which could affect the yield of PCR products. We tested 30, 35, and 40 cycles, respectively. The results showed that 30 cycles produced an insufficient amount fluorescent intensity. In 40 cycles the blank showed some signal of fluorescence. As the results, 35 cycles was selected as the best optimized condition (FIG. 5).

Optimization of the Concentration of $Cu^{2+}$ Ion

Figure 6:
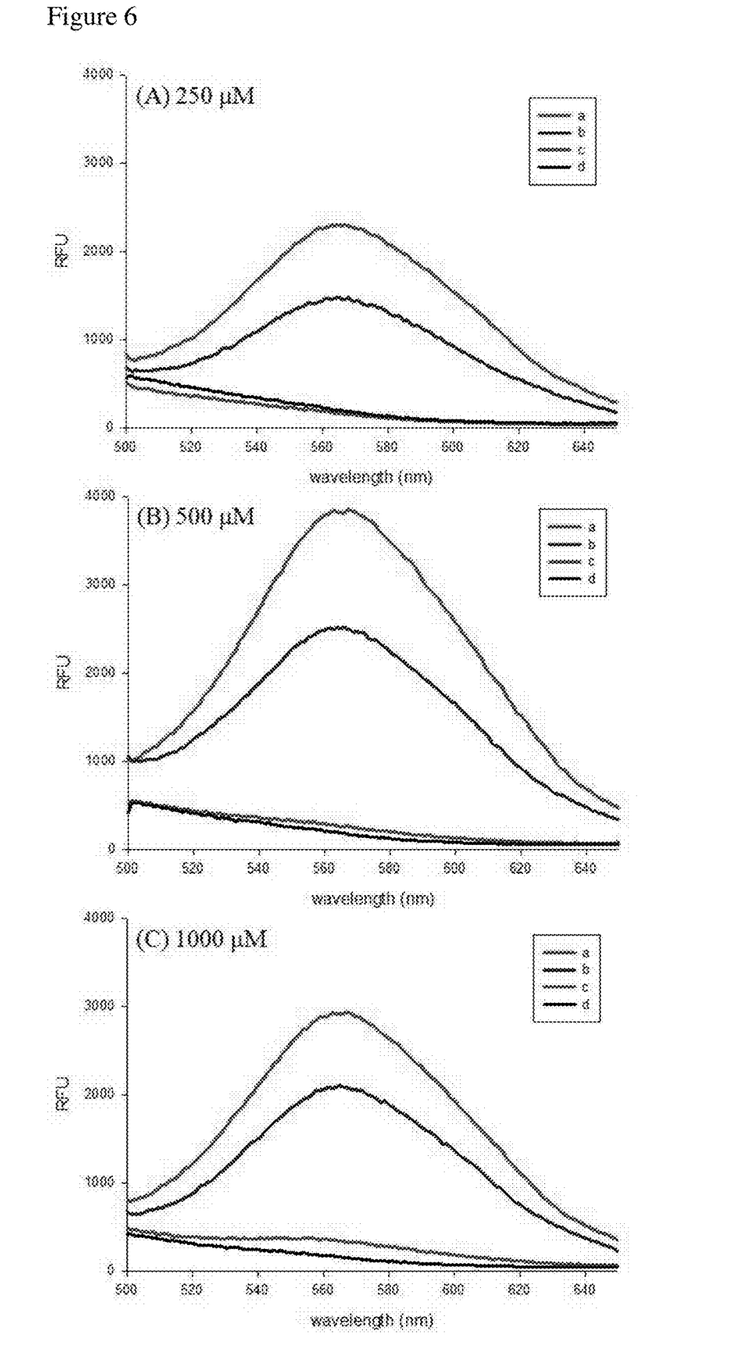
FIG. 6 shows impact of concentration of $Cu^{2+}$ on the fluorescence of the dsDNA-CuNCs. (A) 250 µM; (B) 500 µM; (C) 1000 µM. (a) Duplication type; (b) Normal type; (c) Deletion type; (d) Blank. Other conditions were same as FIG. 2.

The effects of $Cu^{2+}$ ion was an important factor affecting the PCR products of fluorescence for dsDNA-CuNCs. Morkhir et al. reported that dsDNA-CuNCs might be formed in these steps: the reaction of reducing copper (II) to copper (I) followed by the disproportionation of copper (I) into copper (II) and copper (0), the latter being clustered on dsDNA producing stable nanoparticles.[1] According to the results, FIG. 6 (A) showed that weak fluorescent signal was acquired when using 250 µM $Cu^{2+}$, and shows no significant differences between 500 µM and 1000 µM $Cu^{2+}$ ion. However, copper(II) complexes have been reported previously to cleave DNA via oxygen-based radicals after activation with are reducing agent.[3] With the concentration of $Cu^{2+}$ higher than 500 µM, $Cu^{2+}$/sodium ascorbate mixture might generate hydroxyl radical causing the destruction of double DNA helix.[1] Therefore, the concentration of 500 µM $Cu^{2+}$ was chosen in all further experiments.

Optimization of the Concentration of Sodium Ascorbate

Figure 7:
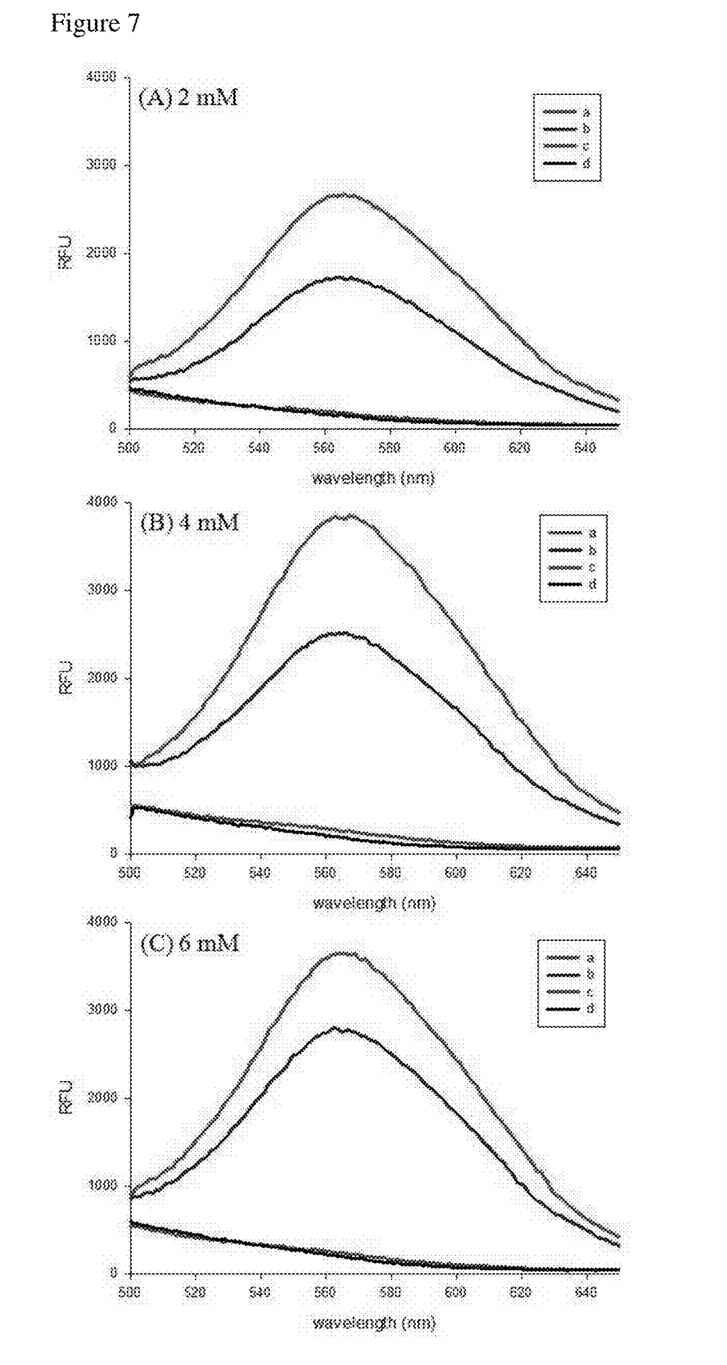
FIG. 7 shows impact of concentration of sodium ascorbate on the fluorescence of the dsDNA-CuNCs. (A) 2 mM; (B) 4 mM; (C) 6 mM. (a) Duplication type; (b) Normal type; (c) Deletion type; (d) Blank. Other conditions were same as FIG. 2.

Due to highly concentrated $Cu^{2+}$/sodium ascorbate mixture, it would generate hydroxyl radicals and lead to the degradation of dsDNA template. The concentration of sodium ascorbate was also investigated. The result was shown in FIG. 7, it was observed that the concentration of sodium ascorbate could achieve the highest fluorescent signal at 4 mM. However, with the concentration of sodium ascorbate higher than 4 mM, the fluorescence intensity decreased with a further increase in concentration of sodium ascorbate. Therefore, 4 mM sodium ascorbate was used in this invention.

Effect of Reaction Time and Performance for dsDNA-CuNCs

Figure 8:
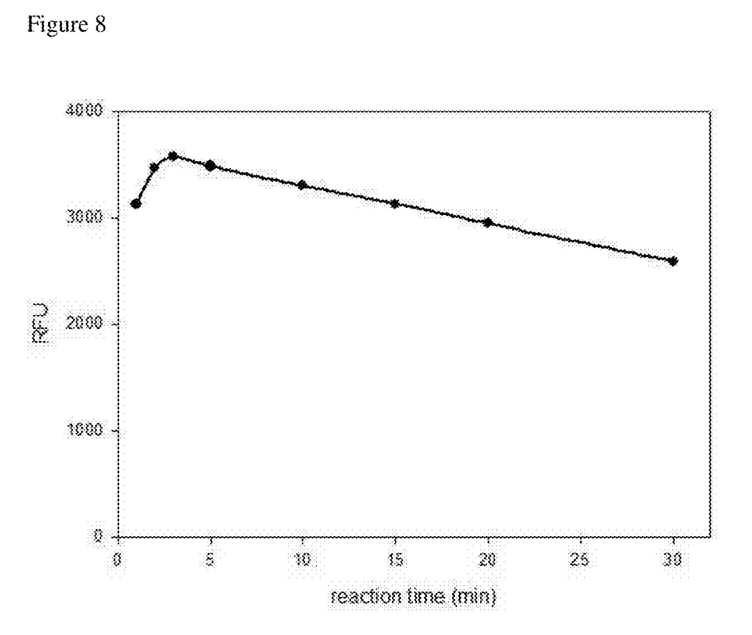
FIG. 8 shows investigation of the stability of CuNCs as a function of reaction time at $\lambda_{em}$=565 nm ($\lambda_{ex}$=345 nm).

To accelerate the detection of PCR products using dsDNA-CuNCs as fluorescent probes, the impact of reaction time between dsDNA and CuNCs on the detection of the exon of normal type was investigated (FIG. 8). The fluorescent intensity reached the maximum peak after 3 min, and began decreasing afterwards. Thus, the reaction time of 3 min was chosen for this study. To distinguish the normal or duplication type of DMD, we could observe in above figure that the fluorescent intensity of duplication type was higher than 600 RFU compared to normal type. These results proved that using dsDNA-CuNCs method for determination the deletion or duplication type of DMD provided a simple method to diagnose the pattern of the fluorescent signal.

Application of Other Exons and the Diagnosis of Real Samples

Figure 9:
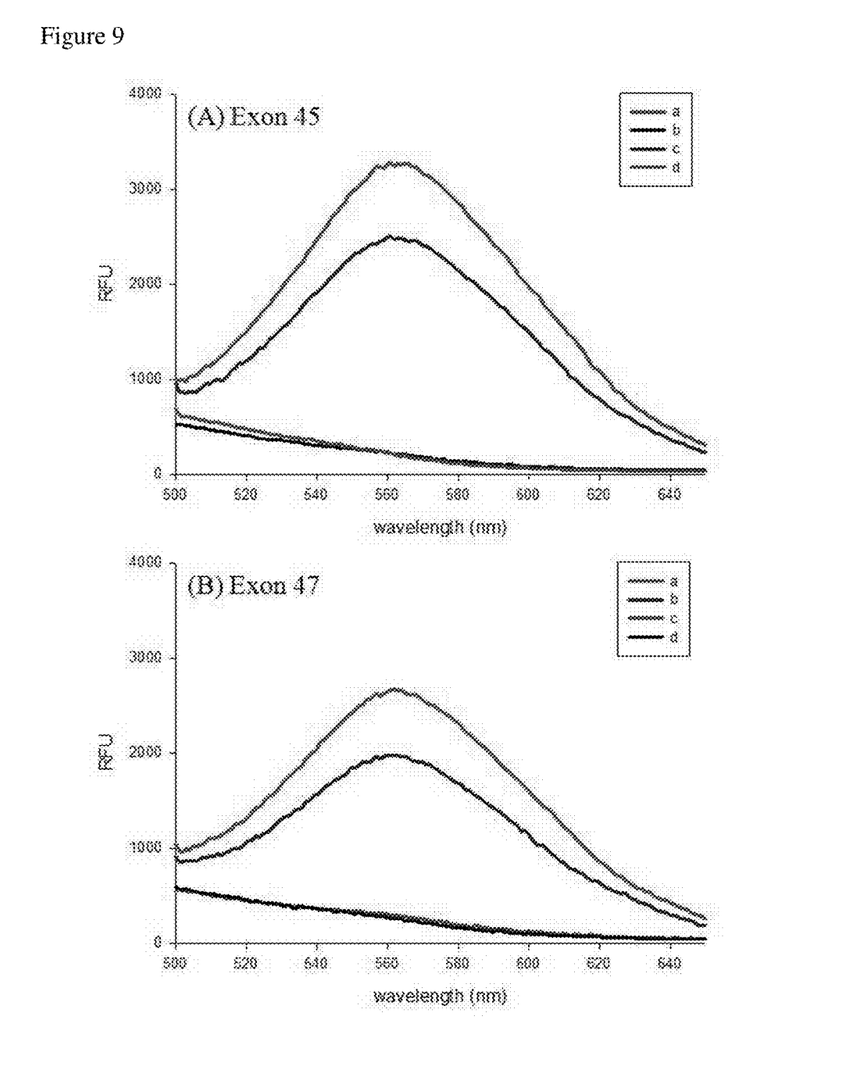
FIG. 9 shows effects of the dsDNA-CuNCs assay for different exons of DMD in clinical test. (A) Exon 45; (B) Exon 47. (a) Duplication type; (b) Normal type; (c) Deletion type; (d) Blank. Other conditions were same as FIG. 2.

To illustrate whether the strategy is applicable to the detection of other exons, we also tested the exon 45 and 47 to demonstrate the design (FIG. 9). Of the 6 clinical samples were acquired from hospitals, all of them had the same results as the MLPA method. The outcomes contained 5 deletion types and 1 duplication type from exon 45 to 47, respectively (Table 1). This result indicated that the method revealed potential for DMD diagnosis.

TABLE 1

Discrepant results of gene type of DMD by MLPA and dsDNA-CuNCs.methods

| Subjects (Patients No.) | MLPA | dsDNA-CuNCs |
| --- | --- | --- |
| 1 | del exon 45-47 | del exon 45-47 |
| 2 | del exon 45-47 | del exon 45-47 |
| 3 | del exon 45-47 | del exon 45-47 |
| 4 | del exon 45-47 | del exon 45-47 |
| 5 | del exon 45-47 | del exon 45-47 |
| 6 | dup exon 45-47 | dup exon 45-47 | del = deletion;
dup = duplication

What is claimed is:

1. An oligonucleotide comprising a nucleotide sequence consisting of SEQ ID NO: 1.

2. A fluorescence-emitting copper nanoparticle which forms from double strands of the oligonucleotide of claim 1 and a solution comprising copper ion with a reducing agent.

3. A method for detecting target DNA in a sample, comprising:
providing a forward primer having a 3' portion that complements a first portion of the target DNA, and a 5' portion comprising a nucleotide sequence consisting of SEQ ID NO: 1; and a reverse primer having a 3' portion that complements a second portion of the target DNA and a 5' portion comprising the nucleotide sequence consisting of SEQ ID NO: 1;

PCR amplifying the target DNA using the forward primer and the reverse primer;

adding a solution comprising copper ion and a reducing agent to a product of the PCR amplification to form a copper nanoparticle with the nucleotide sequence consisting of SEQ ID NO: 1, which results in fluorescence emission; and detecting the fluorescence emission.

4. The method of claim 3, wherein the solution comprising copper ion is $CuSO_4$ solution.

5. The method of claim 3, wherein the reducing agent is sodium ascorbate.

6. The method of claim 3, wherein the target DNA is an exon of a target gene.

\* \* \* \* \*